(12) United States Patent
Stowell Laurence et al.

(10) Patent No.: US 8,252,595 B2
(45) Date of Patent: Aug. 28, 2012

(54) METAL ABSTRACTION PEPTIDE (MAP) TAG AND ASSOCIATED METHODS

(75) Inventors: Jennifer Ann Stowell Laurence, Lawrence, KS (US); Anthony Andrew Vartia, Lawrence, KS (US); Mary Elizabeth Krause, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 13/429,167

(22) Filed: Mar. 23, 2012

(65) Prior Publication Data

US 2012/0177580 A1      Jul. 12, 2012

Related U.S. Application Data

(63) Continuation of application No. 13/341,223, filed on Dec. 30, 2011, which is a continuation of application No. 12/465,448, filed on May 13, 2009, now Pat. No. 8,110,402.

(60) Provisional application No. 61/052,918, filed on May 13, 2008.

(51) Int. Cl.
*G01N 33/00* (2006.01)
(52) U.S. Cl. ............................. 436/86; 436/81; 424/9.34
(58) Field of Classification Search .................. 436/86, 436/81; 424/9.34
See application file for complete search history.

(56) References Cited

U.S. PATENT DOCUMENTS

| | | | |
|---|---|---|---|
| 4,732,864 A * | 3/1988 | Tolman | ......................... 424/1.45 |
| 5,137,819 A | 8/1992 | Kilburn et al. | |
| 5,202,247 A | 4/1993 | Kilburn et al. | |
| 5,225,180 A | 7/1993 | Dean et al. | |
| 5,340,731 A | 8/1994 | Kilburn et al. | |
| 5,443,816 A | 8/1995 | Zamora et al. | |
| 5,496,934 A | 3/1996 | Shoseyov et al. | |
| 5,654,272 A | 8/1997 | Dean | |
| 5,679,548 A * | 10/1997 | Barbas et al. | ................. 435/69.6 |
| 5,837,814 A | 11/1998 | Shoseyov et al. | |
| 5,951,964 A | 9/1999 | Dean et al. | |
| 5,997,844 A | 12/1999 | Dean et al. | |
| 6,057,367 A | 5/2000 | Stamler et al. | |
| 6,074,627 A | 6/2000 | Dean et al. | |
| 6,228,373 B1 | 5/2001 | Bergstrand et al. | |
| 6,274,552 B1 | 8/2001 | Tamarkin et al. | |

(Continued)

FOREIGN PATENT DOCUMENTS

EP          0184355 B1      1/1992

(Continued)

OTHER PUBLICATIONS

U.S. Appl. No. 13/341,223, filed Dec. 30, 2011, Laurence et al.

(Continued)

*Primary Examiner* — Jill Warden
*Assistant Examiner* — Dwan A Gerido
(74) *Attorney, Agent, or Firm* — Wilson Sonsini Goodrich & Rosati

(57) ABSTRACT

Compositions comprising a tripeptide having the sequence $XC_1C_2$; wherein X is any amino acid such that $XC_1C_2$ is capable of binding a metal in a square planar orientation or square pyramidal orientation or both; and wherein $C_1$ and $C_2$ are the same or different; and wherein $C_1$ and $C_2$ individually are chosen from a cysteine and a cysteine-like nonnatural amino acid, as well as metal-$XC_1C_2$ complexes and methods for forming such complexes.

20 Claims, 6 Drawing Sheets

Structure 1

Structure 2

Structure 3

U.S. PATENT DOCUMENTS

| | | | |
|---|---|---|---|
| 6,291,247 | B1 | 9/2001 | Riopelle et al. |
| 6,319,401 | B1 | 11/2001 | Josic et al. |
| 6,331,285 | B1 | 12/2001 | Sharma |
| 6,407,208 | B1 | 6/2002 | Chen et al. |
| 6,537,520 | B1 | 3/2003 | Rajopadhye et al. |
| 6,664,305 | B2 | 12/2003 | Jungbauer et al. |
| 6,736,973 | B1 | 5/2004 | Podgornik et al. |
| 7,052,673 | B2 | 5/2006 | Rajopadhye et al. |
| 7,135,605 | B2 | 11/2006 | Acey et al. |
| 7,238,340 | B1 | 7/2007 | Mcbride et al. |
| 7,592,304 | B2 | 9/2009 | Bar-or |
| 7,632,803 | B2 | 12/2009 | Bar-or |
| 7,973,008 | B2 | 7/2011 | Bar-or |
| 8,017,728 | B2 | 9/2011 | Bar-or et al. |
| 8,110,402 | B2 | 2/2012 | Laurence et al. |
| 2002/0061599 | A1 | 5/2002 | Elling et al. |
| 2003/0035774 | A1 | 2/2003 | Adjei et al. |
| 2003/0055003 | A1 | 3/2003 | Bar-Or et al. |
| 2003/0060408 | A1 | 3/2003 | Bar-Or et al. |
| 2003/0096870 | A1 | 5/2003 | Stamler et al. |
| 2003/0130185 | A1 | 7/2003 | Bar-Or et al. |
| 2003/0207815 | A1 | 11/2003 | Stamler et al. |
| 2004/0002081 | A1 | 1/2004 | Urthaler et al. |
| 2004/0109853 | A1 | 6/2004 | Mcdaniel |
| 2004/0265908 | A1* | 12/2004 | Acey et al. .................. 435/7.1 |
| 2005/0002861 | A1 | 1/2005 | Krause et al. |
| 2005/0226813 | A1 | 10/2005 | Bonasera et al. |
| 2006/0115514 | A1 | 6/2006 | Gengrinovitch |
| 2009/0136594 | A1 | 5/2009 | McLeroy et al. |
| 2010/0213411 | A1 | 8/2010 | Hosoya |
| 2011/0097742 | A1 | 4/2011 | Yang et al. |
| 2011/0212902 | A1 | 9/2011 | Bar-Or |
| 2011/0212903 | A1 | 9/2011 | Bar-Or |
| 2012/0040915 | A1 | 2/2012 | Mukhopadhyay et al. |
| 2012/0088848 | A1 | 4/2012 | Deming et al. |

FOREIGN PATENT DOCUMENTS

| | | |
|---|---|---|
| EP | 1078072 B1 | 1/2007 |
| WO | WO 92/18166 A1 | 10/1992 |
| WO | WO 95/04753 A1 | 2/1995 |
| WO | WO 95/10185 A1 | 4/1995 |
| WO | WO 96/40223 A1 | 12/1996 |
| WO | WO 96/40789 A1 | 12/1996 |
| WO | WO 97/06824 A2 | 2/1997 |
| WO | WO 97/18826 A1 | 5/1997 |
| WO | WO 97/18827 A1 | 5/1997 |
| WO | WO 97/06824 A3 | 7/1997 |
| WO | WO 97/33627 A2 | 9/1997 |
| WO | WO 97/33877 A1 | 9/1997 |
| WO | WO 97/33627 A3 | 2/1998 |
| WO | WO 00/43791 A2 | 7/2000 |
| WO | WO 00/43791 A3 | 7/2001 |
| WO | WO 2005/004842 A2 | 1/2005 |
| WO | WO 2005/004842 A3 | 4/2005 |
| WO | WO 2006/014673 A2 | 2/2006 |
| WO | WO 2006/054904 A2 | 5/2006 |
| WO | WO 2006/014673 A3 | 8/2006 |
| WO | WO 2006/054904 A3 | 4/2007 |

OTHER PUBLICATIONS

U.S. Appl. No. 13/350,247, filed Jan. 13, 2012, Laurence et al.
U.S. Appl. No. 13/428,864, filed Mar. 23, 2012, Laurence et al.
U.S. Appl. No. 13/429,052, filed Mar. 23, 2012, Laurence et al.
Ackerman, et al. Structural and spectral studies of copper(II) and nickel(II) complexes of pyruvaldehyde mixed bis{N(4)-substituted thiosemicarbazones}. Polyhedron. 1999; 18(21):2759-2767.
Adams, et al. New biarsenical ligands and tetracysteine motifs for protein labeling in vitro and in vivo: synthesis and biological applications. J Am Chem Soc. May 29, 2002;124(21):6063-76.
Andersen, et al. Molecular mechanisms of in vivo metal chelation: implications for clinical treatment of metal intoxications. Environ Health Perspect. Oct. 2002;110 Suppl 5:887-90.
Andersen. Principles and recent developments in chelation treatment of metal intoxication. Chem Rev. Sep. 8, 1999;99(9):2683-710.
Bal, et al. Induction of oxidative DNA damage by carcinogenic metals. Toxicol Lett. Feb. 28, 2002 ;127(1-3):55-62.

Bryngelson, et al. Nickel Superoxide Dismutase. Metal Ions in Life Sciences. 2007; 2:417-443.
Cherifi, et al. Transition metal complexes of L-cysteine containing di- and tripeptides. J Inorg Biochem. Jan. 1990;38(1):69-80.
Chivers, et al. Regulation of high affinity nickel uptake in bacteria. Ni2+-Dependent interaction of NikR with wild-type and mutant operator sites. J Biol Chem. Jun. 30, 2000 ;275(26):19735-41.
Chohan, et al. Ligand oxidations in high-spin nickel thiolate complexes and zinc analogues. Inorg Chem. Nov. 29, 2004;43(24):7726-34.
Christlieb, et al. Ligands for molecular imaging: the synthesis of bis(thiosemicarbazone) ligands. Chemistry. Aug. 16, 2006;12(24):6194-206.
Chung, et al. A high-affinity metal-binding peptide from *Escherichia coli* HypB. J Am Chem Soc. Oct. 29, 2008;130(43):14056-7. Epub Oct. 4, 2008.
Cowley, et al. Fluorescence studies of the intra-cellular distribution of zinc bis(thiosemicarbazone) complexes in human cancer cells. Chem Commun (Camb). Feb. 21, 2005;(7):845-7. Epub Jan. 21, 2005.
Coyle, et al. Metallothionein: the multipurpose protein. Cell Mol Life Sci. Apr. 2002;59(4):627-47.
Desoize, et al. Particular aspects of platinum compounds used at present in cancer treatment. Crit Rev Oncol Hematol. Jun. 2002;42(3):317-25.
Donaldson, et al. Structural characterization of proteins with an attached ATCUN motif by paramagnetic relaxation enhancement NMR spectroscopy. J Am Chem Soc. Oct. 10, 2001;123(40):9843-7.
Fernandez, et al. Structure, function, and inhibition of chemokines. Annu Rev Pharmacol Toxicol. 2002;42:469-99.
Fiedler, et al. Spectroscopic and computational studies of Ni Superoxide dismutatse: Electronic structure contributions to enzymatic function. J Am Chem Soc. Apr. 20, 2005;127(15):5449-62.
Gao, et al. CAAX-box protein, prenylation process and carcinogenesis. Am J Transl Res. May 25, 2009;1(3):312-25.
Glennon, et al. Nickel(II) transport in human blood serum. Studies of nickel(II) binding to human albumin and to native-sequence peptide, and ternary-complex formation with 1-histidine. Biochem J. 1982; 203:15-23.
Green. Copper-62 radiopharmaceuticals for diagnostic imaging with positron emission tomography (PET). Transition Met. Chem. 1997; 22:427-429.
Harford, et al Amino Terminal Cu(II)- and Ni(II)-Binding (ATCUN) Motif of Proteins and Peptides: Metal Binding, DNA Cleavage, and Other Properties. Acc. Chem. Res. 1997; 30:123-130.
Heinrich, et al. A square-planar di-N-carboxamido, dithiolato-cobalt(III) complex related to nitrile hydratase metallic site. Addition of axial ligands and EXAFS study of the derived dicyano and diisocyanido complexes. Inorganica Chimica Acta. 2001; 318:117-126.
Hiltunen. Search for new and improved radiolabeling methods for monoclonal antibodies. A review of different methods. Acta Oncol. 1993;32(7-8):831-9.
Hiromura, et al. Intracellular metal transport proteins. Trends in New Element Research. 2001; 35:23-25.
Holland, et al. Functionalized bis(thiosemicarbazonato) complexes of zinc and copper: synthetic platforms toward site-specific radiopharmaceuticals. Inorg Chem. Jan. 22, 2007;46(2):465-85.
International search report dated Oct. 13, 2009 for PCT Application No. US09/43821.
Islam, et al. HAD, a Data Bank of Heavy-Atom Binding Sites in Protein Crystals: a Resource for use in Multiple Isomorphous Replacement and Anomalous Scattering Acta Cryst. (1998) D54, 1199-1206.
Jalilian, et al. Development of [67Ga]2-acetylpyridine 4,4-dimethyl thiosemicarbazone for detection of malignanciesy. Journal of Labelled Compounds and Radiopharmaceuticals. 2007; 50;414-415.
Jang, et al. Metal Ion Complexation by Peptide Monolayer formed on Au Electrodes Asian Chemical Congress Program, Aug. 25, 2005.
Jin, et al. DNA cleavage by copper-ATCUN complexes. Factors influencing cleavage mechanism and linearization of dsDNA. J Am Chem Soc. Jun. 15, 2005 ;127(23):8408-15.
Kelland. The resurgence of platinum-based cancer chemotherapy. Nat Rev Cancer. Aug. 2007;7(8):573-84. Epub Jul. 12, 2007.

Kim, et al. Mixed Bis(thiosemicarbazone) Ligands for the Preparation of Copper Radiopharmaceuticals: Synthesis and Evaluation of Tetradentate Ligands Containing Two Dissimilar Thiosemicarbazone Functions. J. Med. Chem. 1997; 40:132-136.

Knipp, et al. Reaction of Zn7metallothionein with cis- and trans-[Pt(N-donor)2C12] anticancer complexes: trans-Pt(II) complexes retain their N-donor ligands. J Med Chem. Aug. 23, 2007;50(17):4075-86, Epub Aug. 1, 2007.

Kovala-Demertzi, et al. Platinum(II) and Palladium(II) Complexes of Pyridine-2-Carbaldehyde Thiosemicarbazone as Alternative Antiherpes Simplex Virus Agents. Bioinorganic Chemistry and Applications 2007; 1-6.

Krause, et al. MAPping the chiral inversion and structural transformation of a metal-tripeptide complex having ni-superoxide dismutase activity. Inorg Chem. Mar. 21, 2011;50(6):2479-87. Epub Jan. 31, 2011.

Krause, et al. Novel tripeptide model of nickel superoxide dismutase. Inorg Chem. Jan. 18, 2010;49(2):362-4.

Kruszynski, et al. [2-Acetylpyridine 1,1-(hexane-1,6-diyl)thiosemicarbazone-j3N,N0,S]chloroplatinum(II). Acta Crystallographica Section E 2005, E61, m2376-m2378.

Kuchar, et al. Biosynthesis of metal sites. Chem Rev. Feb. 2004;104(2):509-25.

Kulon, et al. Specific interactions of metal ions with Cys-Xaa-Cys unit inserted into the peptide sequence. J Inorg Biochem. Nov. 2007;101(11-12):1699-706. Epub Apr. 19, 2007.

Kumar, et al. Evaluation of an 111In-radiolabeled peptide as a targeting and imaging agent for ErbB-2 receptor expressing breast carcinomas. In Cancer Res. Oct. 15, 2007;13(20):6070-9.

Laurence, et al. Effect of N-terminal truncation and solution conditions on chemokine dimer stability: nuclear magnetic resonance structural analysis of macrophage inflammatory protein 1 beta mutants. Biochemistry. Jun. 30, 1998;37(26):9346-54.

Leach, et al. The role of complex formation between the *Escherichia coli* hydrogenase accessory factors HypB and SlyD. J Biol Chem. Jun. 1, 2007;282(22):16177-86. Epub Apr. 10, 2007.

Lobana, et al. Bonding and structure trends of thiosemicarbazone derivatives of metals—An overview. Coordination Chemistry Reviews. 2009; 253:977-1055.

Mal, et al. The ATCUN domain as a probe of intermolecular interactions: application to calmodulin-peptide complexes. J Am Chem Soc. Nov. 27, 2002;124(47):14002-3.

Maroney, et al. Theoretical Study of the Oxidation of Nickel Thiolate Complexes by O(2). Inorg Chem. Feb. 14, 1996;35(4):1073-1076.

Maroney. Structure/function relationships in nickel metallobiochemistry. Curr Opin Chem Biol. Apr. 1999;3(2):188-99.

Martinez-Huitle, et al. Electrochemical behaviour of dopamine at covalent modified glassy carbon electrode with L-cysteine: preliminary results. Materials Research. 2009; 2(4):375-384.

Maurer, et al. Studies on the mechanism of hypoxic selectivity in copper bis(thiosemicarbazone) radiopharmaceuticals. J Med Chem. Mar. 28, 2002;45(7):1420-31.

Morier-Teissier, et al. Synthesis and antitumor properties of an anthraquinone bisubstituted by the copper chelating peptide Gly-Gly-L-His. J Med Chem. Jul. 23, 1993;36(15):2084-90.

Murray, et al. Axial Coordination of Monodentate Ligands with Nickel(III) Peptide Complexes. Inorg. Chem. 1982; 21:3501-3506.

Nielson, et al. Distinct metal-binding configurations in metallothionein. J Biol Chem. May 10, 1985;260(9):5342-50.

Odenheimer, et al. Rractions of Cisplatin with Sulfur-containing amino acids and peptides I. Cysteine and Glutathione. Inorganica Chimica Acta. 1982; 66:L41-L43.

Ott, et al. Preclinical and clinical studies on the use of platinum complexes for breast cancer treatment. Anticancer Agents Med Chem. Jan. 2007;7(1):95-110.

Pasini, et al. Some aspects of the reactivity of amino acids coordinated to metal ions. J. inorg. nucl. Chem. 1974; 36:2133-2144.

Sakurai, et al. Interaction of Copper(II) and Nickel(II) with L-Histidine and Glycylglycyl-L-histidine as an Albumin Model. Inorg. Chem. 1980; 19:847-853.

Scheinberg, et al. Tumor imaging with radioactive metal chelates conjugated to monoclonal antibodies. Science. Mar. 19, 1982;215(4539):1511-3.

Schmidt, et al. Solution structure of a functional biomimetic and mechanistic implications for nickel superoxide dismutases. Chembiochem. Sep. 1, 2008;9(13):213546.

Scott, et al. Medicinal inorganic chemistry approaches to passivation and removal of aberrant metal ions in disease. Chem Rev. Oct. 2009;109(10):4885-910.

Shearer, et al. A nickel superoxide dismutase maquette that reproduces the spectroscopic and functional properties of the metalloenzyme. Inorg Chem. Mar. 20, 2006;45(6):2358-60.

Shively. Metal Ion Complexes for Antibody Imaging and Therapy in Breast Cancer. 2002.

Shullenberger, et al. Design and Synthesis of a Versatile DNA-Cleaving Metallopeptide Structural Domain. JACS. 1993; 115:11038-11039.

Sigel, et al. Coordinating Properties of the Amide Bond: Stability and Structure of Metal Ion Complexes of Peptides and Related Ligands. Chem. Rev., 1982, 82 (4), pp. 385-426.

Smith, et al. Effect of Nickel(II) and Cobalt(III) and Other Metal Ions on the Racemization of Free and Bound L-Alaninel JACS. 1983; 105:293-295.

Takahara, et al. Crystal structure of double-stranded DNA containing the major adduct of the anticancer drug cisplatin. Nature. Oct. 19, 1995;377(6550):649-52.

Thauer. Nickel to the fore. Science. 2001; 2931:264-1265.

Thilakaraj, et al. In silico identification of putative metal binding motifs. Bioinformatics. Feb. 1, 2007;23(3):267-71. Epub Dec. 5, 2006.

Torrado, et al. Exploiting polypeptide motifs for the design of selective cu(II) ion chemosensors. JACS. 1998; 120:609-610.

Vila, et al. Cylometallated semicarbazone complexes of palladium(II). Crystal and molecular structure of [{Pd[C6H4C(Et)=NN(H)C(=O)NH2]}2(m—Ph2P(CH2)3PPh2)][C1O4]2. Journal of Organometallic Chemistry. 1998; 556:21-30.

Walsh, et al. Protein posttranslational modifications: the chemistry of proteome diversifications. Angew Chem Int Ed Engl. Dec. 1, 2005;44(45):7342-72.

Wierzba, et al. Production and properties of a bifunctional fusion protein that mediates attachment of vero cells to cellulosic matrices. Biotechnol Bioeng Jul. 20, 1995; 47(2):147-54.

Wuerges, et al. Crystal structure of nickel-containing superoxide dismutase reveals another type of active site. Proc Natl Acad Sci U S A. Jun. 8, 2004;101(23):8569-74. Epub Jun. 1, 2004.

Xuan, et al. Formation of Some Cysteine-Containing Peptide Monolayers on Au Electrodes and Their Applications for Metal Ion Sensing and Electrocatalytic Reactions. Bull. Korean Chem. Soc. 2008;29(7):1301-1302.

Yang, et al. Sub-ppt detection limits for copper ions with Gly-Gly-His modified electrodes. Chem Common (Camb). Oct. 7, 2001;(19):1982-3.

Yokoyama, et al. Mononuclear and Binuclear complexes of 99mTc. Int J Appl Radiat Isot. Oct. 1982;33(10):929-36.

Zhang, et al. A role for S1yD in the *Escherichia coli* hydrogenase biosynthetic pathway. J Biol Chem. Feb. 11, 2005;280(6):4360-6. Epub Nov. 29, 2004.

Zoroddu, et al. Molecular Mechanisms in Nickel Carcinogenesis: Modeling Ni(II) Binding Site in Histone H4. Environ Health Perspect. Oct. 2002;110 Suppl 5:719-23.

Zoroddu, et al. Multidimensional NMR spectroscopy for the study of histone H4-Ni(II) interaction. Dalton Trans. Jan. 21, 2007;(3):379-84. Epub Dec. 5, 2006.

Mendieta, et al. Complexation of cadmium by the C-terminal hexapeptide Lys-Cys-Thr-Cys-Cys-Ala from mouse metallothionein: study by differential pulse polarography and circular dichroism spectroscopy with multivariate curve resolution analysis. Analytica Chimica Acta. 1999; 390 (1-3):15-25.

Pietersz, et al. Preclinical characterization and in vivo imaging studies of an engineered recombinant technetium-99m-labeled metallothionein-containing anti-carcinoembryonic antigen single-chain antibody. J Nucl Med. Jan. 1998;39(1):47-56.

* cited by examiner

FIGURE 1

Structure 1

Structure 2

Structure 3

—NCC—

(SEQ ID No: 4) PRL-1 KYRPKMRLRF KDSNGHRNNC CIQ 173

(SEQ ID No: 5) PRL-2 KYRPKMRLRF RDTNGH---C CVQ 167

(SEQ ID No: 6) PRL-3 KYRPKQRLRF KDPHTHKTRC CVM 173

SEQUENCE LISTING

<160> NUMBER OF SEQ ID NOS: 7

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      PCR primer C170S

<400> SEQUENCE: 1
ggtcatagaa acaactcttg cattcaataa ggatc                              35

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      PCR primer C171S

<400> SEQUENCE: 2
ggtcatagaa acaactgttc cattcaataa ggctgtaact c                       41

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      PCR primer H166A -continued

```
<400> SEQUENCE: 3
cgtttcaaac attccaacgg tgctagaaac aactgttgca ttc                    43

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      C-terminus of Human PRL-1 enzyme peptide

<400> SEQUENCE: 4

Lys Tyr Arg Pro Lys Met Arg Leu Arg Phe Lys Asp Ser Asn Gly His
1               5                   10                  15

Arg Asn Asn Cys Cys Ile Gln
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      C-terminus of Human PRL-3 enzyme peptide

<400> SEQUENCE: 5

Lys Tyr Arg Pro Lys Met Arg Leu Arg Phe Arg Asp Thr Asn Gly His
1               5                   10                  15

Cys Cys Val Gln
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      C-terminus of Human PRL-3 enzyme peptide

<400> SEQUENCE: 6

Lys Tyr Arg Pro Lys Gln Arg Leu Arg Phe Lys Asp Pro His Thr His
1               5                   10                  15

Lys Thr Arg Cys Cys Val Met
            20

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 7

Asn Xaa Glu Gln Val Ser Pro
1               5
```

METAL ABSTRACTION PEPTIDE (MAP) TAG AND ASSOCIATED METHODS

CROSS-REFERENCE TO RELATED APPLICATION

This application is a continuation under 35 USC 120 of U.S. Ser. No. 13/341,223, filed Dec. 30, 2011, which is a continuation under 35 USC 120 of U.S. Ser. No. 12/465,448, filed May 13, 2009, now U.S. Pat. No. 8,110,402, issued Feb. 7, 2012, which claims priority to U.S. Provisional Application 61/052,918 filed on May 13, 2008, each of which are incorporated by reference in their entirety.

STATEMENT OF GOVERNMENT INTEREST

The present invention was developed under a grant from National Institutes of Health (Grant No. P20 RR-17708). The U.S. Government may have certain rights to the invention.

SEQUENCE LISTING

This disclosure includes a sequence listing submitted as a text file pursuant to 37 C.F.R. §1.52(e)(v) named 41861701304SeqListing.txt, created on Mar. 23, 2012, with a size of 2.44 kb, which is incorporated herein by reference.

BACKGROUND

Previously, it has been a common technique to utilize metals to extract polypeptides (e.g., proteins or protein fragments) from compositions. Such extraction has been based on the ability of a metal to complex with a specific polypeptide over other substances within the composition. It is known that two different peptide-based metal binding tags can be used for separating a peptide from a composition. However, these binding tags have specific types of amino acids, and specific numbers or specific sequences of amino acids that are utilized to accomplish binding that are substantially different from those described in connection with the present invention. For example, these two binding tags may not bind the same types of metals or bind using the same geometry as the present invention. Additional information regarding the first binding tag can be obtained in U.S. Pat. No. 7,208,138 B2 by Haroon et al., and pertains to a peptide comprising the sequence NXEQVSP (SEQ ID No: 7). Information regarding the second binding tag can be obtained in U.S. patent application publication 2004/0018974 by Arbogast, et al., and pertains to a sequence of the tag that appears to be the entire protein described therein.

Tags that can be encoded in the genetic material of an organism for recombinant expression of proteins have been utilized extensively for purification and identification of protein products. The most noteworthy example of this has been the His-tag technology, which provides a facile means of effectively isolating the tagged protein from whole cells using immobilized metal affinity chromatography (IMAC). Numerous other peptide-based tags have been developed for detecting a tagged protein in cell culture assays or cell lysates using antibodies that recognize the peptide tag. These technologies are useful in in situ or in vitro assays, but they generally are not applicable to in vivo analysis. The advantage of a peptide tag is that the tag is covalently attached to the protein of interest without the need for additional chemical steps to label the protein.

MRI imaging is a common method for examining structural features in live animals and humans. The technology is safe and non-invasive. Contrast agents have been developed to improve the sensitivity of the method, and they are used to enhance the features observed in the MRI image. The improvement is achieved because contrast agents contain metals that alter the signal from neighboring molecules, typically water. The most commonly used agents chelate Gd(III), but other metals can be used to enhance contrast. Gd-containing contrast agents cannot be used in patients with compromised kidney function, as serious complications known as Nephrogenic Systemic Fibrosis or Nephrogenic Fibrosing Dermopathy can result. Alternative imaging agents are needed to address the needs of such patients. Compounds that chelate metals are also used in PET and SPECT imaging to view molecular level details.

SUMMARY

The present disclosure generally relates to tripeptide motifs and methods of using such motifs. These peptides have the ability to bind to metals, which makes them useful for a variety of applications. In particular, the tripeptides of the present disclosure have applications in imaging, research, chemotherapy, and chelation therapies.

According to certain embodiments, the present disclosure provides compositions comprising a tripeptide having the sequence $XC_1C_2$; wherein X is any amino acid such that $XC_1C_2$ is capable of binding a metal in a square planar orientation or square pyramidal orientation or both; and wherein $C_1$ and $C_2$ are the same or different; and wherein $C_1$ and $C_2$ individually are chosen from a cysteine and a cysteine-like nonnatural amino acid.

According to other embodiments, the present disclosure provides compositions comprising a tripeptide having the sequence $XC_1C_2$ and a metal; wherein the metal is complexed with the tripeptide; and wherein X is any amino acid such that tripeptide and metal form a complex having a square planar orientation or square pyramidal orientation or both; and wherein $C_1$ and $C_2$ are the same or different; and wherein $C_1$ and $C_2$ individually are chosen from a cysteine and a cysteine-like nonnatural amino acid.

According to other embodiments, the present disclosure provides methods comprising complexing with a metal a tripeptide having the sequence $XC_1C_2$ to form a metal-$XC_1C_2$ complex; wherein X is any amino acid such that metal-$XC_1C_2$ complex has a square planar orientation or square pyramidal orientation or both; and wherein $C_1$ and $C_2$ are the same or different; and wherein $C_1$ and $C_2$ individually are chosen from a cysteine and a cysteine-like nonnatural amino acid.

The features and advantages of the present invention will be readily apparent to those skilled in the art upon a reading of the description of the embodiments that follows.

DRAWINGS

A more complete understanding of this disclosure may be acquired by referring to the following description taken in combination with the accompanying figures.

FIG. 6 shows A) Electronic absorption spectra of PRL-1 variants purified in the presence of $Ni^{2+}$ ion. Three (two) spectra for each protein variant were recorded from 800 to 200 nm and averaged. Protein concentration for all variants is 5 mg/mL to within 10% based on A280 comparison. Shown are the spectra from 700 to 300 nm. Visible features are absorbance maxima at 318 and 421 nm. Inset. The spectra from 600 to 400 nm are shown at smaller scale for visualization of absorption maxima at 421 and 526 nm. Curves are as follows: PRL-1-WT, black (top); PRL-1-H166A, red (next to top); PRL-1-C170S-C171S, orange (bottom); PRL-1-C170S, green (next to bottom); PRL-1-C171S, blue (middle). B) Resolved spectrum of PRL-1 WT. Resolution of the UV-Vis spectrum of Ni-purified PRL-1 WT protein between 300 and 700 nm fits the data using 5 curves. The 318 nm shoulder is resolved into peaks at 306, 325, and 372 nm. The sum of the resolved absorbance peaks (gray dashed line) and the raw data (solid black line) are both shown. The peaks at 421 and 526 nm are also present.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present invention generally relates to short peptide motifs and methods of using such motifs. These peptides have the ability to selectively bind to metals, which makes them useful for a variety of applications. In particular, the peptides of the present invention have applications in imaging, research, chemotherapy, and chelation therapies.

Generally, the present disclosure is related to short, novel peptide motifs that strongly bind with a select metal, referred to as MAP tag(s). As such, these MAP tags can be used, among other things, to extract the select metal from a composition. The MAP tags of the present disclosure are 3 amino acids in length, and may be included in longer polypeptides and proteins at the N-terminus, C-terminus, or any position in between. In certain embodiments, however, it may be advantageous for the MAP tag to be present in a polypeptide or protein configuration that presents the MAP tag for binding with a metal, such as being present in an external loop. The MAP tag also may be attached to a non-peptide entity. Additionally, more than one MAP tag may be present on a particular molecule.

It is known that many proteins bind metals. However, such binding typically utilizes discontinuous sequences of amino acids within a folded protein structure to accomplish tight binding, which upon unfolding then easily release the metal. On the other hand, metal binding by MAP tags is accomplished using atoms in very close proximity, and as such, extreme conditions are required to release the metal. Thermal and chemical denaturation of the protein permits slow release of the metal. For example, use of extreme conditions (e.g. boiling temperature, strong acid) may lead to slow release of the metal over a period of time (e.g., several to many hours).

A. Chemical Structure

In certain embodiments, the present disclosure provides a novel peptide-based tag or binding agent for a metal (a MAP tag). The MAP tag can be used to directly encode a high-affinity metal binding site in polypeptides or proteins. The MAP tags of the present disclosure are characterized by their ability to bind metals in a square planar and/or square pyramidal geometry.

1. Peptide Sequence

The MAP tags of the present disclosure generally comprise at least three contiguous amino acid residues capable of binding a metal. The MAP tags of the present disclosure generally have a sequence represented by $XC_1C_2$, in which $C_1$ and $C_2$ may be the same or different and may be a cysteine, or a cysteine-like nonnatural amino acid (e.g., a sulfur containing alpha- or beta-amino acid), and in which X may be another natural or nonnatural amino acid or amino acid analogue, so long as the peptide tag formed is capable of binding a metal in square planar/pyramidal geometry. As used herein, the abbreviations for the L-enantiomeric amino acids are conventional and are as follows:

TABLE 1

Abbreviations of the natural amino acids.

| Amino acid | One letter symbol | Three letter symbol |
| --- | --- | --- |
| alanine | A | Ala |
| arginine | R | Arg |
| asparagine | N | Asn |
| aspartic acid | D | Asp |
| cysteine | C | Cys |
| glutamic acid | E | Glu |
| glutamine | Q | Gln |
| glycine | G | Gly |
| histidine | H | His |
| isoleucine | I | Ile |
| leucine | L | Leu |
| lysine | K | Lys |
| methionine | M | Met |
| phenylalanine | F | Phe |
| proline | P | Pro |
| serine | S | Ser |
| threonine | T | Thr |
| tryptophan | W | Trp |
| tyrosine | Y | Tyr |
| valine | V | Val |

In some embodiments, X may be asparagine (N), glutamine (Q), histidine (H), lysine (K), or arginine (R).

When an amino acid sequence is represented as a series of three-letter or one-letter amino acid abbreviations, it will be understood that the left-hand direction is the amino terminal direction and the right-hand direction is the carboxy terminal direction, in accordance with standard usage and convention.

The MAP tag of the present disclosure can be encoded in line with a gene or nucleotide sequence for expression using any recombinant technology system. Additionally, it can be incorporated into a peptide or protein using any synthetic or biosynthetic method for peptide or protein production. In application, the MAP tag spontaneously reacts with a metal to form a peptide-metal complex. Such peptide-metal complexes may form in solution or via transmetallation or any other process.

The MAP tag can be used alone or as a tag that can be attached to the N-terminus, C-terminus or inserted into a flexible linker or loop within a polypeptide chain. The MAP tag can be modified at any position other than at the side chains involved in metal coordination. Accordingly, the MAP tag may comprise sequences such as $Z-XC_1C_2-Z^1$, Z may be any amino acid or any sequence of amino acids, and $Z^1$ may be any amino acid or sequence of amino acids that is equivalent or not equivalent to Z. The amino acids are represented as in above Table 1. Non-natural and amino acids analogues are not listed in the table, but they may be incorporated into Z, $Z^1$, and/or X.

In certain embodiments, the MAP tag may be attached to another molecule. For example, the MAP tag may be attached to a non-peptide entity like a carbohydrate (e.g., hyaluronic acid). The attachment may be covalent, and may be affected through a linker.

In some embodiments, the MAP tag may comprise a sequence as follows: $NC_1C_2$; $Z-NC_1C_2-Z^1$; $Z-NC_1C_2$; $NC_1C_2-Z^1$; $QC_1C_2$; $Z-QC_1C_2-Z^1$; $Z-QC_1C_2$; $QC_1C_2-Z^1$; $HC_1C_2$; $Z-HC_1C_2-Z^1$; $Z-HC_1C_2$; $HC_1C_2-Z^1$; $KC_1C_2$; $Z-KC_1C_2-Z^1$; $Z-KC_1C_2$; $KC_1C_2-Z^1$; $RC_1C_2$; $Z-RC_1C_2-Z^1$; $Z-RC_1C_2$; or $RC_1C_2-Z^1$. As above, Z may be any amino acid or any sequence of amino acids, and $Z^1$ may be any amino acid or sequence of amino acids that is equivalent or not equivalent to Z. The amino acids are represented as in above Table 1. Non-natural and amino acids analogues are not listed in the table, but they may be incorporated into compounds Z and $Z^1$.

In one embodiment, the MAP tag comprises NCC having the following structural formula:

In certain embodiments, a MAP tag of the present disclosure may be encoded in line with a gene or nucleotide sequence that provides for targeted delivery of the MAP tag, either before MAP tag complexation with a metal or after complexation with a metal. This may be accomplished using genes, peptides, or other motifs known to be useful for targeting. For example, MAP tags may be incorporated with an antibody, growth factors, peptides, and the like.

2. Metal Binding

In certain embodiments, the MAP tags of the present disclosure, alone or when incorporated into a polypeptide or protein, may complex with a metal to form a MAP tag-metal complex having a square planar/pyramidal geometry. The metal may complex with the MAP tag through 2N:2S coordination. The MAP tags also may bind a number of metals in a square planar geometry under suitable conditions that will be appreciated by one of ordinary skill in the art. In general, the MAP tags of the present disclosure may bind, referring to IUPAC Group: Group 3 metals, such as Y; Group 5 metals, such as V and U; Group 6 metals, such as Cr, Mo, W; Group 7 metals such as Mn, Tc, Re; Group 8 metals, such as Fe and Ru; Group 9 metals, such as Co, Rh, Ir; Group 10 metals such as Ni, Pd, Pt; Group 11 metals, such as Cu, Ag, Au; Group 12 metals, such as Zn, Cd, Hg; Group 13 metals, such as Al, Ga, In, Tl; Group 14 metals, such as Sn and Pb; and Group 15 metals, such as Bi. In certain embodiments, the MAP tag may bind and form a MAP tag-metal complex with Zn, Ni, Cu Pt, Pd, Au, Ag, Pb, and Fe.

As mentioned above, upon binding the metal, the MAP tag has a square planar geometry. The present disclosure also contemplates MAP tag metal coordination in a variety of square planar configurations. For example, when the MAP tag is NCC and the metal is any metal as described above, and represented as M, the MAP tag may have a structural formula represented by Formula 1:

Formula 1

Other structural configurations are also contemplated. For example, when the MAP tag is $NC_1C_2$ and $C_1$ is a nonnatural amino acid, such as (S)-2-amino-2-mercaptoacetic acid and $C_2$ is cysteine, the MAP tag's structural formula may be represented as Formula 2, in which M is any metal as described above:

Formula 2

In another example, the MAP tag is $NC_1C_2$ and $C_2$ is a non-natural amino acid, such as (S)-2-amino-4-mercaptobutanoic acid, the MAP tag's structural formula may be represented as Formula 3, in which M is any metal as described above:

Formula 3

In another example, the MAP tag is $NC_1C_2$ and $C_2$ is a β amino acid, such as 3-amino-2-mercaptopropanoic acid, the MAP tag's structural formula may be represented as Formula 4, in which M is any metal as described above:

Formula 4

In another example, the MAP tag is RCC and the MAP tag's structural formula may be represented as Formula 5, in which M is any metal as described above:

Formula 5

In another example, the MAP tag is QCC and the MAP tag's structural formula may be represented as Formula 6, in which M is any metal as described above:

Formula 6

B. Applications of the MAP Tag

1. MAP Tags for Metal Abstraction

As mentioned above, a MAP tag is capable of binding metals with high affinity. A MAP tag is also capable of abstracting a metal from various compositions ranging from fluids to solids. Consequently, the ability of MAP tags to abstract the metal, rather than share coordination, make them amenable for use in separating a specific metal from another composition, as described more fully below. The MAP tag sequesters a metal ion from compositions by complexing with the metal and then abstracting or removing the metal from a component in the composition, such as a chelating agent (e.g., EDTA) or a solid support conjugated with, for example, IDA or NTA. As such, the MAP tag is a metal abstraction peptide (MAP) tag.

Additionally, due at least in part, to a MAP tag's ability to selectively bind to metals, embodiments of the present disclosure may be useful for chelation therapy. Thus, a MAP tag may be used to sequester a biologically toxic metal, such as lead.

Similarly, MAP tags also may be useful in sequestering metals from water, other aqueous solutions, or any compositions outside of the body. The MAP tag itself is generally soluble in numerous solvents. However, in certain embodiments, the MAP tag-metal complex is poorly soluble in many organic solvents and may precipitate once metal binding occurs. This allows for efficient separation during the extraction from an organic solvent.

2. Imaging Applications

In certain embodiments, the present disclosure provides methods for imaging using a MAP tag. Such methods may be used for therapeutic and medical imaging, or for other imaging applications. The metal chosen to be complexed with the MAP tag will depend on the particular application and imaging technique. For examples, a paramagnetic metal may be chosen for use with imaging techniques such as MRI, NMR and EPR, while gold may be chosen for techniques such as electron microscopy, while zinc may be chosen for applications such as fluorescence. Which metals are suitable for a given application and imaging technique are well-known to those skilled in the art.

In one embodiment, a MAP tag is utilized to prepare a reagent for use in imaging techniques. That is, a MAP tag is bound to a metal, which in turn provides a complex that can be used for imaging (e.g., used in a body of a subject such that the metal can be use for imaging). Examples of suitable imaging techniques include, alone or in combination, Computed Tomography (CT), Magnetic Resonance Imaging (MRI), ultrasound, Positron Emission Tomography (PET), Single Photon Emission Computed Tomography (SPECT), Nuclear Magnetic Resonance (NMR), Electron Paramagnetic Resonance (EPR), electron microscopy, fluorescence imaging, and the like.

In another embodiment, a MAP tag may be incorporated into a polypeptide or protein, or non-protein entity that localizes to a portion of a subject, where the metal portion of a MAP tag-metal complex provides the ability to image the site of localization, such as a tissue or tumor. For example, the MAP tag-metal complex can be used to identify a tissue or other structure expressing a receptor and/or binding partner to the targeting portion of the MAP-tagged molecule. Imaging techniques that can visualize the metal can be used for the identification of such features.

For example, MRI contrast agents are paramagnetic species, typically containing a metal center, that alter the relaxation of neighboring atoms to generate a difference in the detected signal between the areas where the contrast agent is present and those where it is not. A MAP tag may be paramagnetic when complexed with Cu. A MAP tag-metal complex therefore has potential for use as a MRI contrast agent. Most contrast agents are not targeted on a microscopic level but are used to reveal macroscopic structures and defects in a body or tissue. In this type of application, the concentration of the contrast agent is very high. Targeting a contrast agent to a selected tissue or microscopic feature is beneficial in that it permits identification of aberrations on the cellular level. For example, the MAP tag may be expressed as a tag on an antibody that recognizes cancer cells expressing a specific receptor. Targeted delivery may allow for a lower concentration of contrast agent to be administered, which, among other things, may help minimize toxicity and other side effects.

It is known that $^{62}$Cu is a radioactive isotope that is used in PET and SPECT imaging, which are capable of imaging molecular details within a body. As such, a MAP tag can be loaded with the appropriate radioisotope of Cu (or another metal) and used as a tracer with these imaging techniques. Similarly, by fusing the tag to any protein or peptide or other molecule that binds a subset of cells, targeted imaging can be accomplished.

The MAP tag is advantageous, among other things, because it is a short sequence with high affinity for certain metals. Thus, by encoding a MAP tag in an expressed protein or other molecule, targeted delivery to a specific cell type within an organism is possible. Further, targeting a subset of cells permits a decrease in the amount of contrast agent needed for imaging.

3. Chemotherapy

The present invention may also be used to aid in chemotherapy. For example, a MAP tag may form a complex with platinum and/or radionucleotides and be used to provide targeted delivery to a particular cell or type of cell.

To facilitate a better understanding of the present invention, the following examples of specific embodiments are given. In no way should the following examples be read to limit, or to define, the entire scope of the invention.

EXAMPLES

Example 1

Mutagenesis techniques were used to identify the peptide motif having the strong binding affinity with select metals. Briefly, the human PRL-1 gene was cloned into pET-30 Xa LIC vector (Novagen) and mutated using the PCR-based QuikChange method (Stratagene). The primers generating the C170S, C171S, and H166A mutants, 5' to 3', were ggtcatagaaacaactCttgcattcaataaggatc (SEQ ID No: 1), ggtcatagaaacaactgttCcattcaataaggctgtaactc (SEQ ID No: 2), and cgtttcaaacattccaacggtGCtagaaacaactgttgcattc (SEQ ID No: 3) (Integrated DNA Technologies, Coralville, Iowa), respectively. Capital letters indicate mutated bases. PCR reactions were treated with DpnI (Promega) for 1.5 h at 37° C., directly transformed into NovaBlue GigaSingles Competent cells (Novagen) and plated on LB with 30 mg/mL kanamycin selection. Individual colonies were grown overnight in selective LB at 37° C. The resultant DNA was purified using the Wizard Plus MiniPrep System (Promega). All mutations were confirmed by DNA dye-terminator sequencing (Northwoods DNA, Inc., Bemidji, Minn.). The double mutant C170S/C171S was produced by a second round of mutagenesis and similarly confirmed.

Vectors containing PRL-1 and relevant mutant genes were transformed into BL21(DE3) cells (Novagen) and grown overnight at 37° C. on selective LB. Selected colonies were grown in selective M9ZB broth overnight at 37° C. Overnight cultures were then transferred to 500 mL unlabeled minimal medium and induced with 1 mM IPTG at an $OD_{550}$ between 0.6 and 0.8. Proteins expressed for NMR experiments were grown in minimal medium containing chloride. Over-expression of the recombinant protein was confirmed by SDS-PAGE. Cells were pelleted by centrifugation at 4400×g and stored at −80° C. until used.

Figure 2:
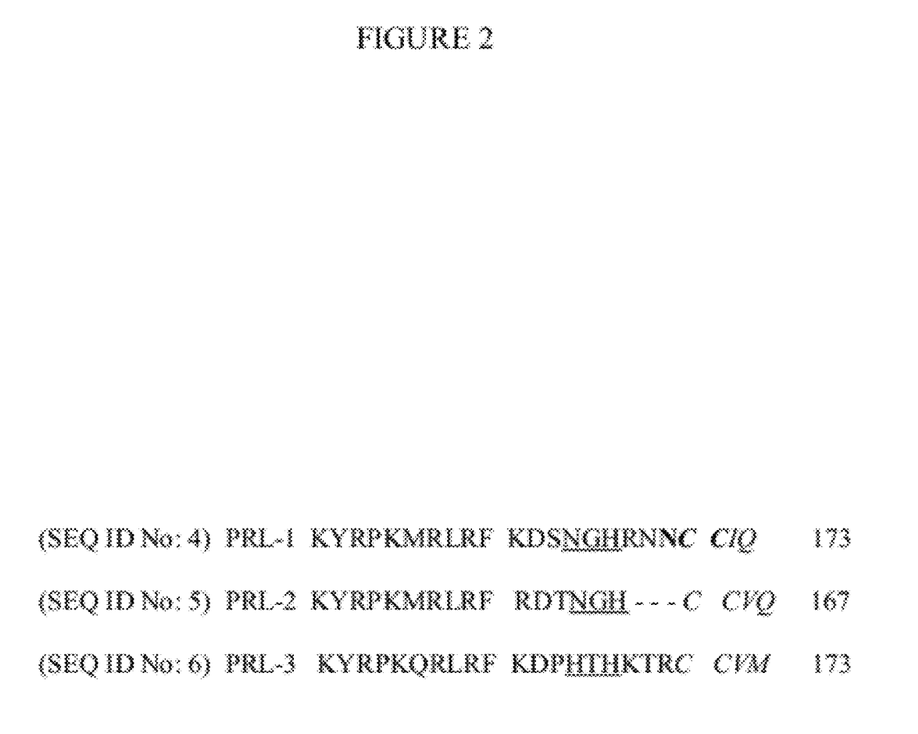
FIG. 2 shows a sequence alignment of the C-terminal portion of human PRL enzymes, including PR1-1, PRL-2, and PRL-3. H166 of PRL-1 is part of the NGH motif shown underlined. Residues C170 and C171 of PRL-1 are part of the CaaX motif shown in italics. The NCC motif is bold.

A series of PRL-1 mutants were examined to identify residues that participate in metal coordination. Model peptides containing a GGH-like motif have been shown to coordinate Ni(II) and Cu(II) with extremely high affinity. In this motif substitution at either of the two Gly positions only modestly decreases binding, whereas mutation of the His abolishes it. PRL-1 encodes NGH, a GGH-like consensus motif, near its C-terminus (FIG. 2). Therefore, PRL-1-H166A was made to test the hypothesis that the NGH sequence contained in PRL-1 is responsible for metal binding. PRL-1 and PRL-1-H166A analyzed by ICP-MS in parallel bound approximately 120 and 60 µM Ni, respectively. Only a 20% decrease in signal was observed for H166A when measured by absorption spectroscopy. It also appears from the absorption spectra that the protein signal is diminished to an equivalent extent and that the loss of signal in the visible region is due to protein instability. Protein instability likely accounts for the disparity in the two detection methods since ICP-MS requires substantially more manipulation of the sample prior to analysis. Because the histidine mutant retained tight binding, mutations at C170 and/or C171 were made because thiols often participate in Ni coordination. Ni levels in individual cysteine mutants, as well as the double mutant, were greatly reduced relative to wild-type protein, indicating both Cys residues influence metal coordination. No Ni was detected in the C170S mutant or the C170S-C171S double mutant, but a small signal of approximately 17 µM was observed for PRL-1-C171S.

Example 2

Protein purification techniques were used to purify the protein-metal complex. Briefly, cell pellets were resuspended in 30 mL buffer A (100 mM NaCl, 50 mM Tris-HCl, 10 mM imidazole, pH 7.4, Ar-sparged) and lysed at 15,000 psi using a French pressure cell (ThermoElectron). Argon sparging of buffers was performed to displace oxygen. Samples then were centrifuged at 21,000×g and the supernatants were filtered through a 0.2 µm nylon filter. Purification of $(His)_6$-tagged PRL-1 was carried out using an Äkta Explorer purification system at a flow-rate of 1 mL/min. Samples were applied to a metal-charged 5 ml HiTrap Chelating Column (GE Healthcare) and rinsed with 5 column volumes after loading. Elution was accomplished using a linear gradient to 60% buffer B (100 mM NaCl, 50 mM Tris-HCl, 500 mM imidazole, pH 7.4, with or without argon sparging) over 13 column volumes, to 100% B over 3 column volumes, and maintained at 100% B for 4 column volumes. Elution was monitored by absorption at 280 nm, and fractions were examined for purity using SDS-PAGE. The appropriate fractions were pooled and dialyzed against Ar-sparged or not sparged 100 mM NaCl, 50 mM Tris-HCl, pH 7.4. The $(His)_6$-tag was cleaved from the target protein using Factor Xa protease (Promega) overnight at room temperature. Protease was removed using Xarrest™ agarose (Novagen) and filtered with a 0.2 µm nylon filter before reapplication to the column to remove the tag and any uncleaved protein. The protein was applied to the column in dialysis buffer and the initial flow-through was collected to make the protein sample. Samples were concentrated and exchanged at least $10^6$-fold in Ar-sparged 100 mM NaCl, 50 mM TrisCl, pH 7.4 using (Amicon Ultra) 10 kDa MWCO centrifugal filters. Purity and mutant verification of the samples were ascertained by SDS-PAGE and ESI-MS, respectively. Columns were treated with 1 M NaOH, stripped with 2 column volumes of 100 mM EDTA and recharged with Ar-sparged 100 mM $NiSO_4$, 100 mM $CuSO_4$, 100 mM $CuCl_2$ or 100 mM $ZnCl_2$ immediately preceding each use.

Figure 5:
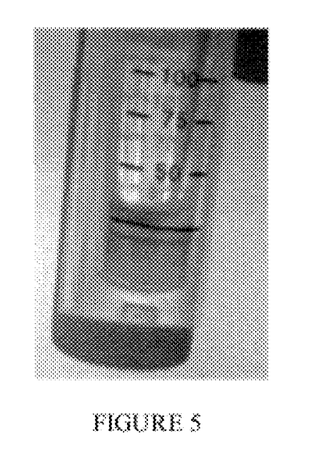
FIG. 5 shows a photograph of purified WT PRL-1 purified in the presence of Ni(II), pH 7.4 after cleavage and removal of the His-tag. Photograph shows its characteristic rust color.

FIG. 5 shows purified PRL-1 after cleavage and removal of the His-tag. Metal bound to the his-tag has octahedral geometry, which is blue-green in color and the absorption corresponding to such a coordination event would appear in the 700-800 nm region of the spectrum. Photograph of WT PRL-1 purified in the presence of Ni(II), pH 7.4 shows its characteristic rust color. The purified wild-type PRL-1 protein has an unexpected rust color (FIG. 5), which could result from metal complexation or oxidation of aromatic residues (i.e., Trp or Tyr).

Oxidation of aromatic residues was easily ruled out based on the mass spectrometry data from the intact and tryptic digest studies of the protein. Moreover, we observed the density of the protein to be higher than expected, as the rust-colored protein becomes concentrated at the bottom of the tube during high-speed centrifugation. As metal coordination would increase the density of the protein complex, we further investigated the possibility that the chromophore is generated by the formation of a metal complex with the protein. Because metal chelation chromatography was used to purify PRL-1, the most likely source of metal ions was Ni from the IMAC resin.

When cell lysate containing recombinant WT PRL-1 is equally divided and purified side-by-side using $Ni^{2+}$-, $Cu^{2+}$- or $Zn^{2+}$-charged IMAC resin, the protein abstracts the metal bound to the chelating resin. The rate of transmetallation is most rapid with nickel, followed by copper. Zinc is present to some extent in all samples, indicating the protein picks up zinc in vivo. When zinc is bound to the column, only zinc is observed in the protein. Apo PRL-1 is poorly soluble and loss of metal leads to precipitation. The soluble material from each purification when tested by inductively coupled plasma mass spectrometry (ICP-MS) has an equivalent proportion of metal bound.

Example 3

ICP-MS was used to characterize the bound metal. Briefly, purified protein samples were digested in concentrated nitric acid in PFA microcentrifuge tubes (Savillex, #s 7240, 7241) at 68±1° C. for 16.5±0.7 hours. Based on protein quantification prior to digestion, the sample was then diluted to 1.5 µM in 20 mM ammonium bicarbonate, pH 8.2, filtered through a 0.2 µm nylon filter, and injected into a VG Elemental VGII+ XS Inductively-Coupled Plasma-Mass Spectrometer fitted with a microconcentric nebulizer. A minimum of two separately prepared samples were analyzed for each protein variant. Each sample was scanned twice and standards were run before, between, and after each sample scan. Drift was monitored during washes between scans of both sample and standard injections.

To investigate our hypothesis that the chromophore arises from protein abstraction of the metal from the charged IMAC matrix, samples were subjected to ICP-MS for semi-quantitative analysis. As extensive washing is used to remove background metals, the values obtained from this method inherently underestimate the amount of metal bound, but can be used to assess the relative affinity of different metals for the protein. Additionally, to identify an endogenous metal ligand that may have been bound to PRL-1 during expression in the cells, ICP-MS was used to look for the presence of a transition metal from the first two rows in the periodic table as well as other common biologically relevant metals. Strikingly, the data showed that PRL-1 bound only to Zn and the specific metal, for example Ni, used on the IMAC column during purification. On average 500 µM Ni-purified protein samples were digested in nitric acid for 16 h at 70° C. were determined to contain approximately 180 µM Ni, yielding a Ni to protein stoichiometry of 1:2.7+/−0.7. Zn was also detected in the Ni-purified samples at approximately 60 µM. Separately, purification of PRL-1 using Zn-IMAC showed Zn was the only metal present in high quantity at 270 µM [1 Zn:1.8 protein], and these protein samples contained only background levels of Ni. ICP-MS of both Ni- and Zn-purified PRL-1 show no other metals in significant quantity, which suggests that zinc is coordinated in vivo and becomes partially displaced by $Ni^{2+}$ during the nickel chromatographic purification. Because ICP-MS analysis is conducted in a flow of Ar and the most abundant isotope of Ar has the same mass as Ca, Ca binding cannot be determined from the primary mass signal. Nonetheless, because a much higher amount of Ca was present in the cell culture media compared to Zn and yet the ICP-MS signal corresponds largely to zinc, the protein is unlikely to bind calcium. The ICP-MS data indicate Zn is present in an appreciable amount when PRL-1 is purified using Ni-IMAC, which suggest that Zn binding occurs in the cell.

Example 4

UV-Vis absorption spectra were used to measure the concentration of the PRL-1 protein. Briefly, the concentrations of purified PRL-1 analogs were measured at 280 nm and calculated using an extinction coefficient of 19420 $M^{-1}$ $cm^{-1}$. Because of possible metal-protein absorption interferences in the high 200 nm region, the validity of the UV-Vis quantification method was confirmed by the Bradford method. Spectra of PRL-1 analogs at concentrations of 10, 5, 2.5, and 1.25 mg/mL were collected on a Cary 100 UV-Vis spectrophotometer from 800 to 200 nm. To correct for scattering effects in the analysis, PRL-1-WT spectra were adjusted by subtracting the PRL-1-C170S-C171S spectrum, because it does not bind metal. The resulting spectra were resolved and peak positions were evaluated using GRAMS/AI 7.00 software. Three methods were aimed at metal displacement. In the first, PRL-1-WT (e.g., wild type) samples were reduced using 20 mM β-mercaptoethanol (BME), and imidazole was added to a concentration of 10 mM. For 0.5 mM protein samples, this corresponds to 400-fold solution excess of BME to compete with the two C-terminal cysteine thiols and a 200-fold solution excess of imidazole to compete with the single C-terminal histidine imidazole side chain. New baselines were taken and the spectra recalculated. In the second method, baselines were recalculated for buffer containing 100 µM EDTA, and the spectrum for the PRL-1-WT sample that was exchanged ten million fold in 100 µM EDTA was recorded. Finally, 10 mg/mL protein samples were denatured in 5.6 M guanidinium hydrochloride and heated to 90° C., new baselines were taken, and the spectra were collected at 0, 2, 4 and 6 hrs.

Figure 6A:
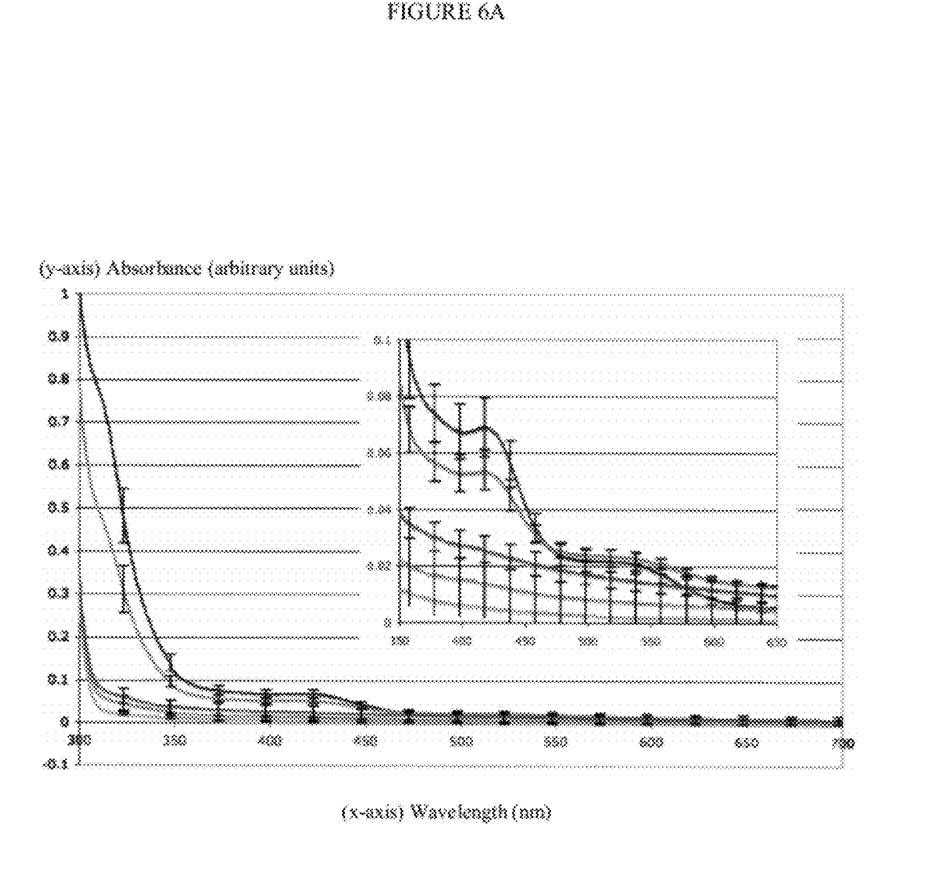

Accordingly, characterization of metal coordination by PRL-1 was determined with UV-Vis absorption spectroscopy. The metal coordination geometry employed by PRL-1 and its mutants was analyzed using UV-Vis absorption spectroscopy at 800-200 nm. Absorption spectra of PRL-1 produced peaks at 280 and 220 nm, which arise from aromatic and peptide bonds within the protein and correspond well with the concentration determined using the Bradford assay. Metal-containing compounds often absorb at several wavelengths in the visible range, and the Ni- and Cu-purified PRL-1 proteins also display peaks in the visible range, which correspond to the rust color of the sample. PRL-1 WT shows a maximum at 318 nm (evident as a shoulder on the very large 280 band), a broader signal at 421 nm, and a very broad peak at 526 nm (FIG. 6A). Cu-purified PRL-1 generates a similar spectral profile Ni purified PR1-1 (data not shown); however, a small blue shift is observed for the individual spectral peaks, which is expected when Cu is substituted for Ni. As expected, no absorption or visible color was observed when the protein was purified using resin charged with Zn. This is due to the fact that Zn(II) has a completed d-shell and as such should not show electronic transitions in the visible spectrum.

Relative to the WT protein, the H166A variant showed the same absorption profile, but the peaks were decreased in intensity to a degree consistent with the ICP-MS results. The spectra of PRL-1-WT and PRL-1-H166A are distinct from those of the cysteine mutants in the visible region. At equivalent concentration, individual substitutions at cysteine 170 and/or 171 with serine show complete loss of signal at 421 and 526 nm. These mutant proteins were examined at concentrations as high as 10 mg/mL (0.5 mM), and no specific absorption bands were detected. Signal from the WT is evident at 0.1 mg/mL, indicating that binding of Ni is decreased by each mutation at least 100-fold.

Figure 6B:
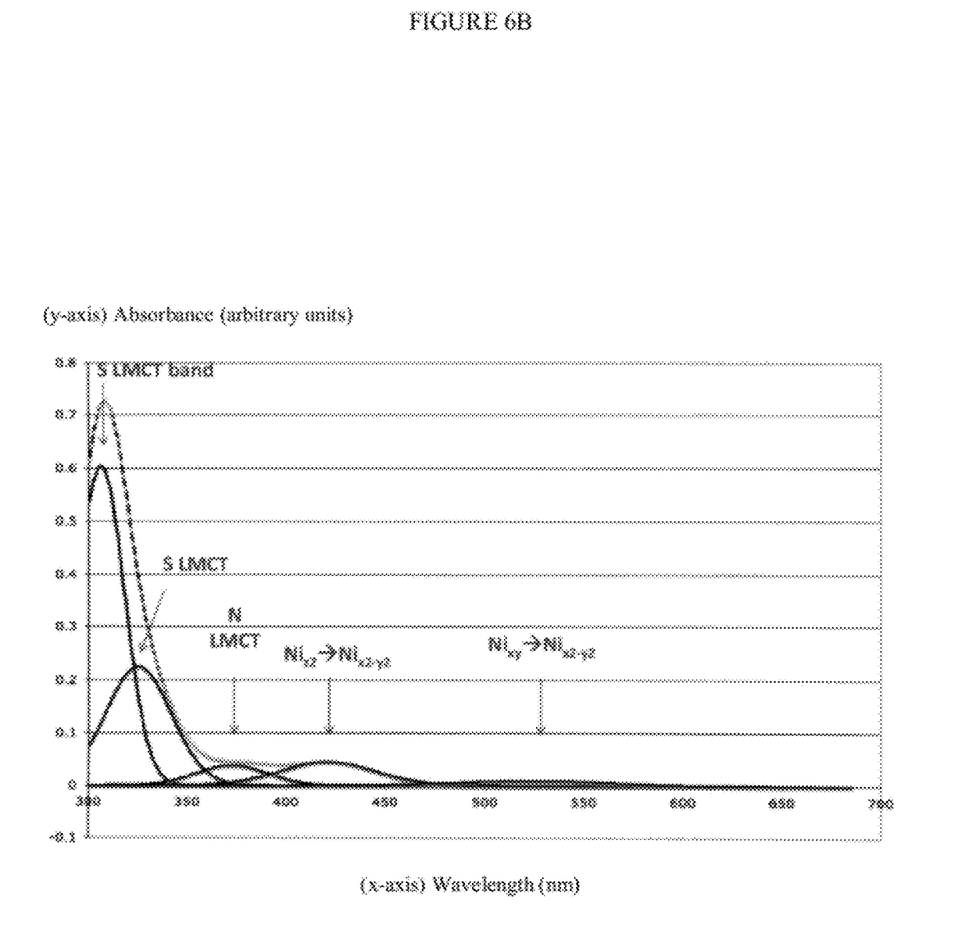

Deconvolution of the UV-Vis spectra of corrected WT protein was performed between 300 and 700 nm and reveals that the 318 nm peak is composed of 3 separate absorbance bands at 306, 325, and 372 nm, respectively contributing 54%, 38% and 7% to the total composite peak absorbance (FIG. 6B). The absorption profile of PRL-1-H166A is highly similar to the wild-type protein spectrum. The absence of the imidazole group at residue 166 does not shift the absorbance maxima or contribute significantly to the component bands of the 318 nm absorption, further indicating that the imidazole from the histidine within the NGH motif does not directly coordinate Ni.

Ni binding in PRL-1 is not affected by reduction of the disulfide bond at PRL-1's active site. Addition of 20 mM BME did not alter the UV or visible region of the spectral absorption profile, indicating that metal binding is largely unaffected by reduction of the protein and the presence of the reducing agent. Subtraction of the reduced spectrum from the oxidized confirms that there is no significant difference in metal coordination between the reduced and oxidized WT samples. To examine whether a small contribution from a His is made, additional imidazole was added to the solution to increase the signal strength of a transient association. Addition of 10 mM imidazole had no effect on the absorption profile, which suggests that access to the Ni is limited. Additionally, no spectral change was observed when the Ni-purified sample was reduced in the presence of imidazole. Ten million-fold exchange of Ni-purified WT sample into buffer containing 100 µM EDTA had little effect on the spectrum, and absorbance values for this sample were within error of the WT absorbance. Raising the pH from 7.4 to 8.5 should increase the molar absorptivity coefficient ($\epsilon$) by approximately 6-fold, but interestingly, no change in $\epsilon$ is observed when the pH is elevated, which may suggest that the bound Ni is solvent inaccessible in PRL-1. Decreasing the pH to 6.5, however, does decrease the intensity of the visible peaks (data not shown).

Ni binding appears to be irreversible at pH 7.4, as displacement of Ni from Ni-purified PRL-1 requires aggressive measures. When Ni-purified PRL-1 was treated with 5.6 M guanidinium hydrochloride at 90° C., the peaks at 318, 421 and 526 nm only gradually disappear over 6 hrs (data not shown). The concomitant appearance of a signal at 750 nm was observed over the 6 hours, which indicates Ni was released from the protein and coordinated by water in octahedral geometry. FIG. 6A shows the electronic absorption spectra of PRL-1 variants purified in the presence of $Ni^{2+}$ ion. Three spectra for each protein variant were recorded from 800 to 200 nm and averaged. Protein concentration for all variants is 5 mg/mL to within 10% based on $A_{280}$ comparison. Shown are the spectra from 700 to 300 nm. Visible features are absorbance maxima at 318 and 421 nm. In FIG. 6A, curves are as follows: PRL-1-WT, black; PRL-1-H166A, red; PRL-1-C170S-C171S, orange; PRL-1-C170S, green; PRL-1-C171S, blue.

FIG. 6B shows a resolved spectrum of PRL-1 WT. Resolution of the UV-Vis spectrum of Ni-purified PRL-1 WT protein between 300 and 700 nm fits the data using 5 curves. The 318 nm shoulder is resolved into peaks at 306, 325, and 372 nm. The sum of the resolved absorbance peaks (gray dashed line) and the raw data (solid black line) are both shown. The peaks at 421 and 526 nm are also present.

The inset of FIG. 6B shows the spectra from 600 to 400 nm are shown at an expanded scale for visualization of absorption maxima at 421 and 526 nm.

Example 5

Electrospray ionization mass spectrometry (ESI-MS) was used to analyze the samples. Briefly, ESI spectra were acquired on a Q-Tof-2 (Micromass Ltd, Manchester UK) Hybrid Mass Spectrometer operated in MS mode and acquiring data with the time of flight analyzer de-tuned to 8000 resolution (FWHH) for sensitivity. For whole protein ESI spectra, purified protein samples were diluted to 1 µg/µL in untreated ("oxidizing") 20 mM ammonium bicarbonate, pH 8.2 and allowed to incubate at room temperature. Time points were taken on the first, fourth, and seventh day post-purification and frozen at −80° C. until ready for use. Samples were desalted on a short (3 cm×1 mm I.D.) reverse-phase (RP) HPLC column (Hamilton PRP1, Reno, Nev.). Samples were loaded onto the column from a 1% formic acid solution with protein (5 µg), washed in same solution, and eluted with 90% MeOH/0.5% formic acid directly into the ESI source. The cone voltage was 60 eV, and the voltage on the collision cell was 20 V. Spectra were acquired over the mass range 800 to 3000 u, accumulating data for 5 seconds per cycle.

For tryptic digests, PRL-1-WT, PRL-1-H166A and PRL-1-C170S-C171S were diluted to 1 mg/mL in ammonium bicarbonate, pH 8.2, with or without 20 mM β-mercaptoethanol, and trypsin (Promega) was added in a 1:50 ratio protease:protein (w/w) and incubated at 37° C. for 16 hrs. To confirm complete digestion, samples at various time points were run on SDS-PAGE and visualized by silver staining Coupled to MS analysis, capillary HPLC separations were performed using a Zorbax SBC18 RP column (5 cm×0.32 mm I.D., 3.5 µm bead size, 300 Å pore size) packed by Micro-Tech Scientific (Sunnyvale, Calif.), with a chromatograph (Waters capLC XL, Milford, Mass.) that develops gradients at 10 µL/min. A linear gradient of 20 to 80% B was applied over 120 minutes. The solvents were: A 99% $H_2O$, 1% MeOH, B 99% MeOH, 1% $H_2O$, both 0.08% formic acid. Argon was admitted to the collision cell at a pressure that attenuates the beam to about 20%. This corresponds to 16 psi on the supply regulator or $5.3 \times 10^{-5}$ mBar on a penning gauge near the collision cell. The collision cell was operated at 8 V for maximum transmission, and spectra were acquired over the range 250 to 2000 u, accumulating data for 8 seconds per cycle.

NMR experiments were conducted to analyze the samples. Briefly, 2D $^1H$-$^{15}N$ HSQC spectra were acquired on a Bruker Avance 800 MHz NMR spectrometer using a cryogenic, triple-resonance probe equipped with pulse field gradients. Water suppression was accomplished using flip-back pulses. All spectra were obtained at 37° C. and acquired in 16 scans with 2048 points in $^1H$. 256 or 128 increments were collected in $^{15}N$ for WT and C170S-C171S, respectively. Samples were prepared in 50 mM sodium phosphate, 100 mM NaCl at pH 6.5 and contained 5% $D_2O$. The concentration of WT PRL-1 and PRL-1-C170S-C171S was 1.0 mM and 0.8 mM, respectively. Sample reduction was accomplished by addition of 10 mM DTT at least 24 hours prior to spectral acquisition. $^1H$ chemical shifts were referenced with respect to an external DSS standard in $D_2O$. Indirect referencing relative to $^1H$ was determined for $^{13}C$ and $^{15}N$, assuming ratios $^{13}C/^1H$=0.251449530 and $^{15}N/^1H$=0.101329118. Computer programs nmrPipe and Sparky were used for data processing and spectral analysis.

Example 6

Figure 3:
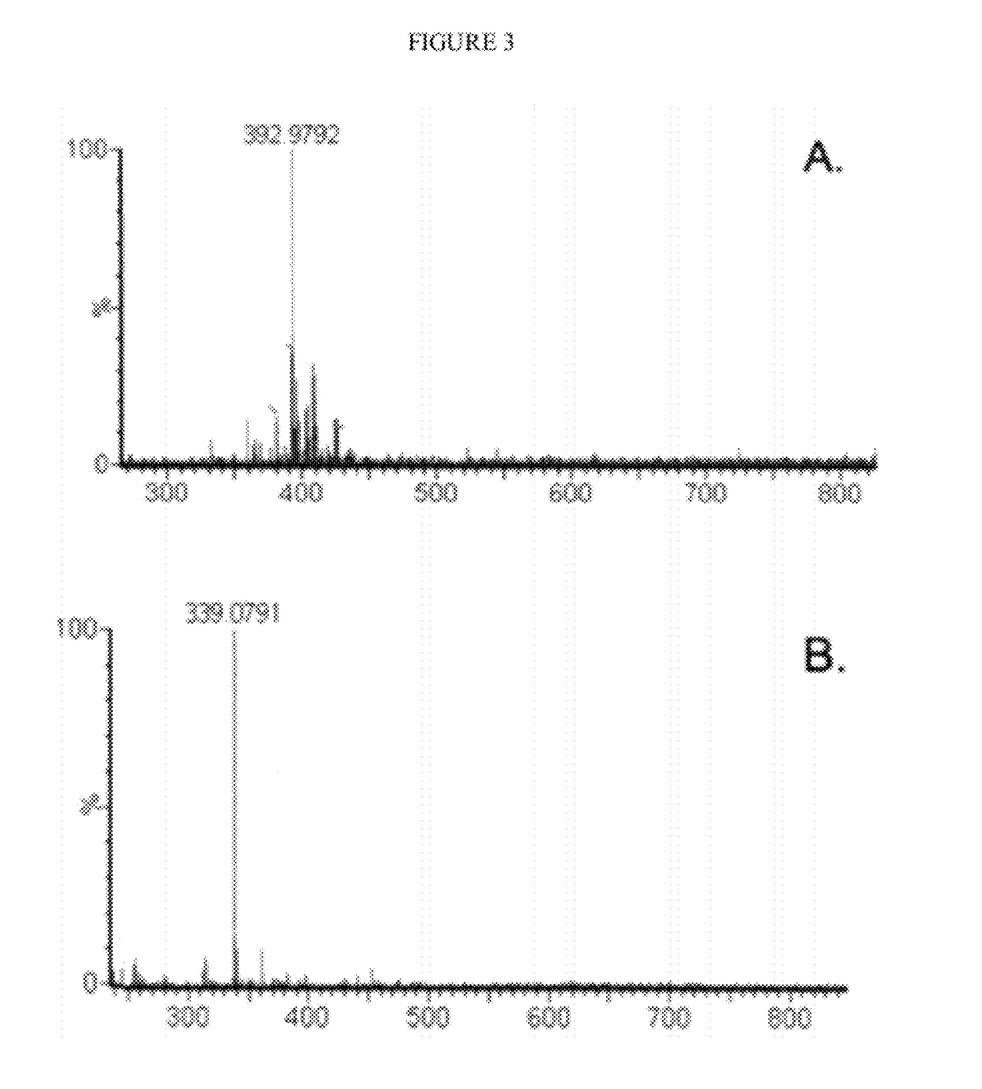
FIG. 3 shows A. ESI-MS of the nickel-bound tripeptide acquired at pH 10, where the mass indicates that nickel is bound to the peptide. B. ESI-MS spectrum after dropping the pH of the sample to 5, showing that nickel has been released from the peptide.

To confirm that the MAP tag motif is entirely responsible for metal binding, we synthesized NCC. The NCC peptide was synthesized and purified, and the peptide was incubated with metal-charged IMAC resin. Complex formation was verified using electrospray ionization mass spectrometry (ESI-MS) operating in negative ion mode (FIG. 3).

Figure 4:
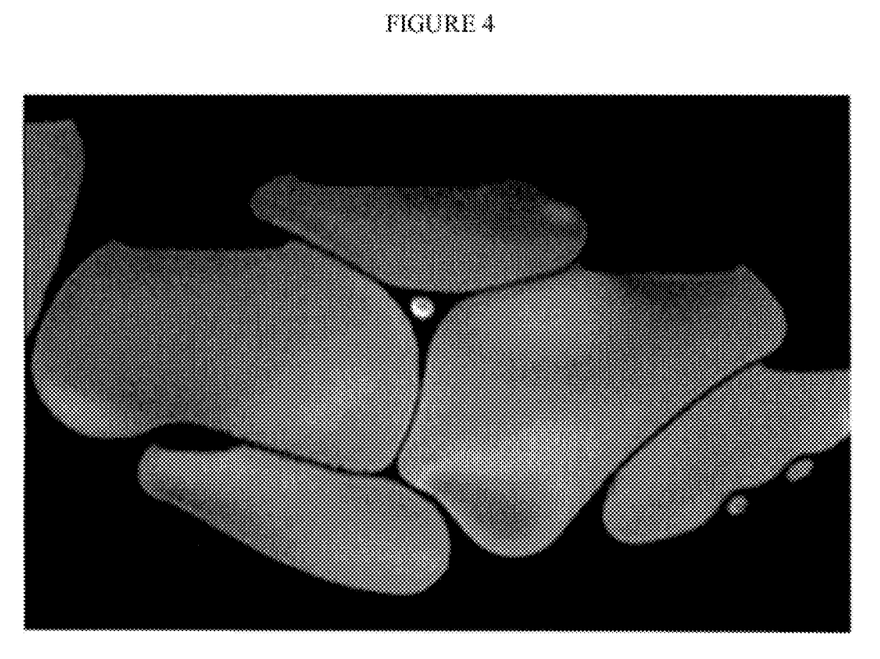
FIG. 4 shows Cu—NCC magnetic resonance image (MRI).

In the NCC peptide, the absorption signal mimics that observed for the peptide-metal complex embedded in PRL-1, but the complex is more exposed in the tripeptide. The absorption in the visible range intensifies when the pH is raised from 6 to 7.4. Acidification diminishes the signal intensity and when returned to the more basic pH, full signal fails to be restored, indicating irreversible loss of some metal from the square planar geometry may occur. Elevation of the pH to 10 suggests a fifth ligand, presumably water or hydroxide, is coordinated, generating a square pyramidal arrangement. At pH 7.4, this ligand is presumably highly exchangeable and too transient to be detected by absorption spectroscopy. The exchangeable ligand provides an avenue for paramagnetic relaxation of the bulk solvent and can be detected by MRI (FIG. 4). Additionally, the metal was added by mixing the metal salt into aqueous solution containing the peptide. Depending on the conditions, the absorption spectrum of the peptide either paralleled the complex formed via metal transfer or was distinctly different from that obtained for the full-length protein. The differing spectrum reveals that the metal may be coordinated solely by sulfur in this case. Although the NCC peptide is sufficient to confer metal binding, the type of complex generated depends on the method by which the metal is introduced to the peptide. Transmetallation provides an efficient pathway for incorporation of the metal into the NCC tripeptide to generate the extremely high affinity square planar complex.

Figure 1:
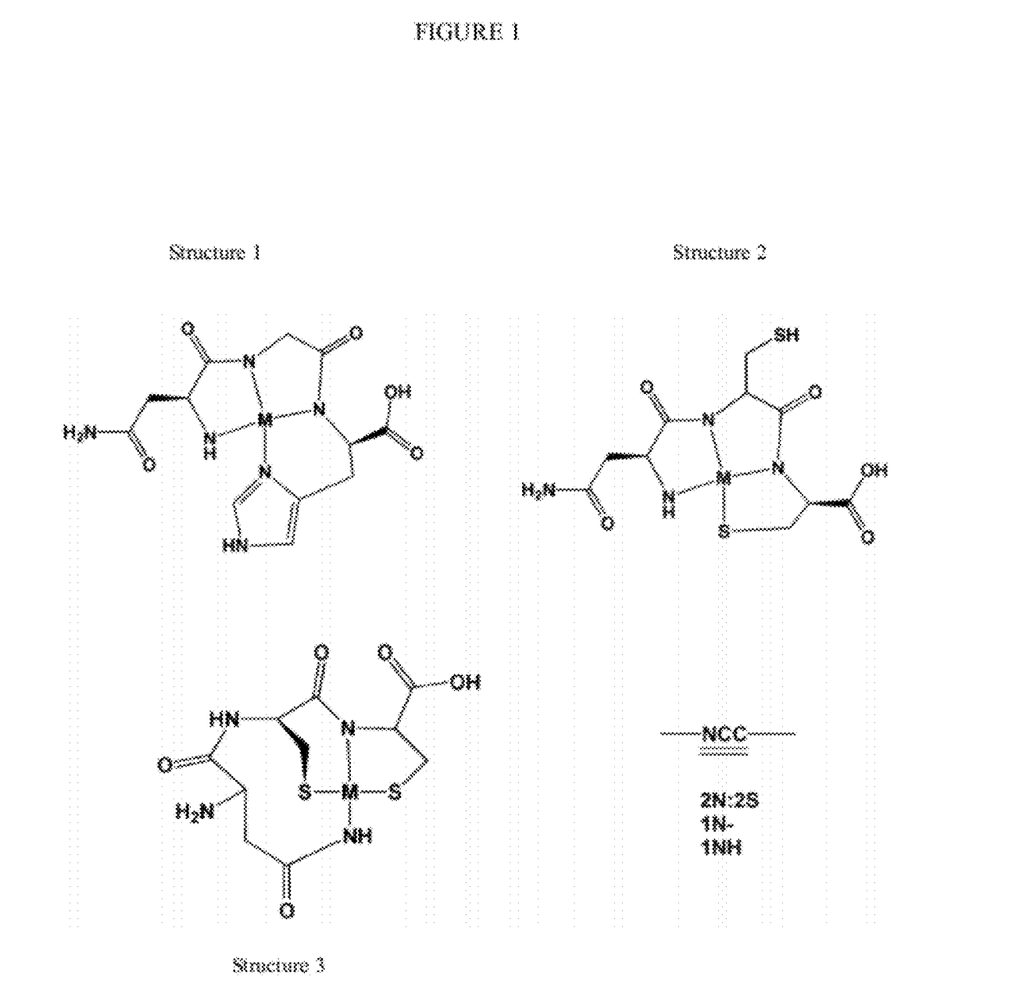
FIG. 1 shows Structure 1—a GGH-like metal complex NGH, with 4N coordination. Structure 2 depicts a GGH-like metal coordination by a NCC peptide, whereas Structure 3 depicts the unique, high-affinity binding arrangement of NCC, involving 2N:2S coordination.

The GGH-like metal complex of NGH is shown in FIG. 1, Structure 1. We envisioned two possible chemical structures for the metal-bound NCC complex, which are shown in FIG. 1, Structure 2 and Structure 3. Structure 2 corresponds to a GGH-like arrangement that involves coordination of the metal by several deprotonated backbone N atoms. In this case, the imidazolium nitrogen from His would be replaced in NCC with the sulfur from the Cys in the third position in the coordinated complex. This complex would have 3N:1S coordination, which is not consistent with our absorption spectra. To verify the unique, specific coordination by NCC, NGC also was synthesized and confirmed the importance of the central Cys side chain in metal binding. The NGC peptide incubated with the IMAC resin does not produce an absorbance spectrum that resembles the metal-bound NCC or PRL-1 spectrum. As such, we concluded that GGH-like coordination is not utilized and must have a much lower affinity for binding metal in the specified geometry.

Structure 3 is completely in line with the data obtained for both the peptide alone and the peptide in the context of the larger protein. The absorption spectrum of both indicate that two sulfur atoms participate in the complex along with two nitrogen atoms, one which is deprotonated and the other which has a single proton attached. Structure 3 may not involve the N-terminal amine group, which would likely cause differences in the spectra of the peptide and protein because this atom would be embedded in a peptide bond in the protein. Based in part on this structure, the nitrogen from Q, H, K, or R may be substitute for N in the first position of the motif.

The metal binding site and coordination geometry was studied. The finding that PRL-1 binds divalent metal cations is interesting because specific metal coordination by other PTPases has not been reported. The C-terminal sequence of PRL-1 is unique among this enzyme family, and it encodes both a GGH-like motif, which in certain cases is able to bind metal, but not in this case, and the novel MAP tag motif The geometry of GGH-like motifs is square planar. The characteristic rust color observed with the concentrated PRL-1 samples parallels the color of the GGH peptides, which suggests that Ni coordination occurs in a square planar geometry. Our studies further reveal that Ni is bound in the C-terminus of PRL-1. Metal coordination is not accomplished by the GGH-like motif in PRL-1 because mutation of the would-be essential His has little affect on binding. Despite the fact that both tripeptides bind using square planar coordination, the chemistry for each is distinct.

UV-Vis spectra derived from Ni-purified WT PRL-1 display bands near 318, 421 and 526 nm. For peptides and organic molecules binding Ni in a square planar geometry via nitrogen ligands, characteristic d-d bands near 420 nm are reported frequently in the literature. Maroney et al. ("Theoretical Study of the Oxidation of Nickel Thiolate Complexes by O(2)." *Inorg Chem.* 1996 Feb. 14; 35(4):1073-1076) performed ab initio calculations and made spectral assignments of synthetic peptide mimetics that coordinate Ni(II) and Cu(II) using square planar geometry. With the exception of a single band, their observations and calculations are in close agreement with the observed spectrum from PRL-1. Separately, the reduced, square-planar form of NiSOD was analyzed using density functional theory, the results of which show similar relevant features. The locations of the bands as well as the trend in their relative intensities in these systems are well preserved in the PRL-1 protein spectrum. Based on these and other studies, it is likely the 526 nm band arises from $Ni_{xy}$-->$Ni_{x2-y2}$ transitions. Similarly, the 421 nm band may come from $Ni_{xz}$-->$Ni_{x2-y2}$ transitions. The strong 318 nm band reflects the ligand-metal charge transfer band (LMCT). Resolution of the spectrum reveals that this absorbance is likely a composite of 3 bands at 306, 325, and 372 nm. Using the other structures as a guide, the sharpest, most intense band at 306 nm would correspond to transitions from sulfur atoms, with the other two bands likely arising from nitrogen donation or possibly weaker sulfur donation.

Within the series of C-terminal mutants, only mutations involving C170 and C171 abolished signal at these wavelengths. Most notably, the 318 nm envelope corresponding to the LMCT is lacking in the cysteine mutant spectra. With respect to the entire absorption profile, the small very broad absorbance in the low 300 nm region for the cysteine mutants appears to be an artifact from high-intensity bands at lower wavelengths or a scattering effect, as it is positioned incorrectly to be one of the 318 nm component bands. The bands attributable to transitions within Ni d-orbitals (421 nm, 526 nm) also are absent when sulfur is substituted by oxygen. The original bands are absent and no additional bands appear upon mutation of either C170 or C171 in the absorption spectra. Also no disulfide bonds involving these residues are observed in the MS data. As such, it seems that both cysteines directly participate in metal coordination. Our ICP-MS data further indicate that both sulfur atoms from C170 and C171 are required for tight Ni-binding, as neither sulfur atom alone appears to be sufficient.

The spectral features generated by PRL-1 also suggest Ni is coordinated by nitrogen atoms in the remaining two positions. Frequently imidazolium N from His or backbone amide N are observed to coordinate metals such as Zn, Cu and Ni. In model peptides and proteins that bind Ni using square planar geometry, some of the ligating nitrogen groups become deprotonated, and the negatively charged species binds the metal. The absorption band at 526 nm indicates that PRL-1 coordinates Ni via a deprotonated nitrogen, whereas the 421 nm absorption generated in the PRL-1 spectrum reflects coordination by a singly protonated nitrogen. Mutations of the His in the GGH-like motif to make PRL-1-H166A revealed that this histidine's side chain does not substantially influence Ni binding. PRL-1 encodes three other His in addition to H166. H23, H64 and H103 are located in distant regions of the sequence and are unlikely to remain tightly associated under denaturing conditions. Attempts to unfold the protein so as to release the metal required vigorous treatment with high concentrations of denaturants at high temperature for several hours. As chemical and heat denaturation permit only slow release of Ni and CD data show that PRL-1 completely unfolds well before Ni is released, the metal is likely coordinated by atoms clustered in a short segment of the protein.

The GGH-type peptides achieve extremely tight binding ($K_d \sim 10^{-17}$-$10^{-18}$), which is accomplished in part by deprotonated backbone amide nitrogens within the motif. In light of the extremely tight binding observed for PRL-1 and the predicted contribution from nitrogen atoms to Ni ligation, backbone amides from PRL-1 may participate in metal coordination. Because the absence of either cysteine abolishes binding and truncation removes both the side chain and the backbone amide, testing the hypothesis that metallation involves the amide nitrogens adjacent to C170 and C171 using mutagenesis is not feasible. Structural studies are the best way to identify the additional coordinating atoms, and these studies are underway in our laboratory.

Example 7

Cu—NCC at physiological pH was placed in a tube surrounded by saline bags and imaged using a standard MRI at the Hoglund Brain Imaging Center at the University of Kansas Medical Center (FIG. 4). In FIG. 4, the bright signal in the center corresponds to the Cu—NCC complex, whereas the less bright signal corresponds to the saline solutions. Black corresponds to the tube and air.

Therefore, the present invention is well adapted to attain the ends and advantages mentioned as well as those that are inherent therein. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference.

What is claimed is:

1. A method of increasing aqueous solubility of a peptide by forming a peptide-metal complex with said peptide and a metal atom or ion, said method comprising
   a) adding said peptide to a metal-containing composition, wherein said peptide includes a sequence $XC_1C_2$, wherein X is any natural or non-natural amino acid or amino acid analog, and further wherein $C_1$ and $C_2$ are each individually chosen from a cysteine and a sulfur-containing alpha or beta amino acid;
   b) forming a peptide-metal complex between said peptide and a metal atom or ion in said metal-containing composition wherein the metal atom or ion is bound in a square planar or square pyramidal orientation; and
   c) formulating said peptide-metal complex into an aqueous composition.

2. The method of claim 1, wherein said peptide is included in the sequence $Z—XC_1C_2—Z_1$, wherein Z and $Z_1$ are each individually any natural or non-atural amino acid or sequence of natural or non-natural amino acids.

3. The method of claim 1, wherein said peptide is included in the sequence $Z—XC_1C_2$, wherein Z is any natural or non-natural amino acid or sequence of natural or non-natural amino acids.

4. The method of claim 1, wherein said peptide is included in the sequence $XC_1C_2—Z_1$, wherein $Z_1$ is any natural or non-natural amino acid or sequence of natural or non-natural amino acids.

5. The method of claim 1, wherein $C_1$ and $C_2$ are each cysteine.

6. The method of claim 1, wherein X is chosen from asparagine, glutamine, histidine, lysine, and arginine.

7. The method of claim 1, wherein said metal-containing composition in step (a) comprises an aqueous solvent.

8. The method of claim 1, wherein said metal-containing composition in step (a) comprises an organic solvent.

9. The method of claim 1, wherein said aqueous composition of step (c) is a therapeutic composition.

10. The method of claim 1, wherein said aqueous composition of step (c) is an imaging composition.

11. The method of claim 1, wherein said metal-containing composition in step (a) comprises a metal atom or ion attached to a solid substrate or support.

12. The method of claim 1, wherein said peptide is contained within a polypeptide or protein sequence.

13. The method of claim 12, wherein said polypeptide or protein sequence is part of an antibody sequence.

14. The method of claim 1, wherein said metal-containing composition further comprises a chelating agent.

15. The method of claim 14, wherein said chelating agent is selected from the group consisting of iminodiacetic acid (IDA) and nitrilotriacetic acid (NTA).

16. The method of claim 1, wherein said peptide is linked to a polypeptide, an antibody, a growth factor, or a carbohydrate.

17. The method of claim 16, wherein said peptide is linked to an antibody.

18. The method of claim 1, wherein said metal is selected from the group consisting of a Group 3 metal, a Group 5 metal, a Group 6 metal, a Group 7 metal, a Group 8 metal, a Group 9 metal, a Group 10 metal, a Group 11 metal, a Group 12 metal, a Group 13 metal, a Group 14 metal, and a Group 15 metal.

19. The method of claim 12, wherein said metal is selected from the group of Group 12 metals consisting of Zn, Cd, and Hg.

20. The method of claim 13, wherein said metal is Zn.

* * * * *